Figure 1:
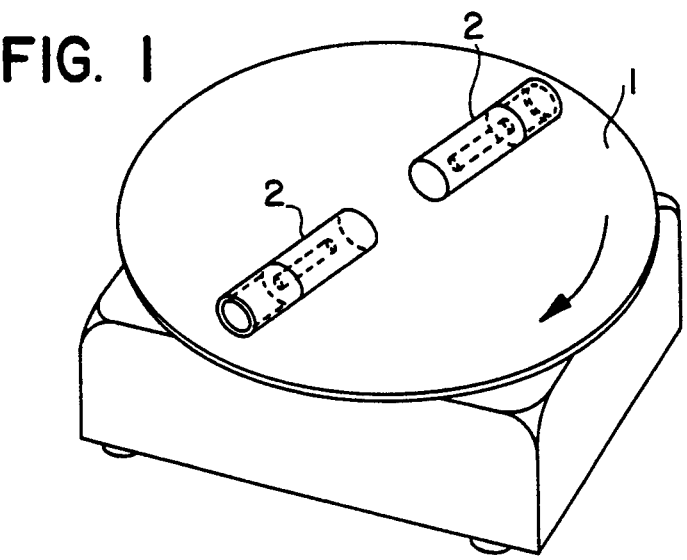

United States Patent [19]

Driessen

[11] Patent Number: 5,256,314
[45] Date of Patent: Oct. 26, 1993

[54] DEVICE AND METHOD FOR THE QUANTITATION OF A VOLUME OF A SEDIMENT OR OF A VOLUME OF A FLUID WHICH DOES NOT FLOW EASILY

[76] Inventor: Oscar M. J. Driessen, Rue de la Forge 23, B-4851 Sippenaeken, Belgium

[21] Appl. No.: 778,939
[22] PCT Filed: Jun. 14, 1990
[86] PCT No.: PCT/NL90/00083
  § 371 Date: Dec. 13, 1991
  § 102(e) Date: Dec. 13, 1991
[87] PCT Pub. No.: WO90/15664
  PCT Pub. Date: Dec. 27, 1990

[30] Foreign Application Priority Data

Jun. 16, 1989 [NL] Netherlands ............... 8901530

[51] Int. Cl.⁵ ............................................. B01D 21/26
[52] U.S. Cl. ........................... 210/787; 210/361; 210/515; 210/516; 210/518; 422/72; 422/101
[58] Field of Search ............... 210/515, 516, 518, 787, 210/361, 222; 422/72, 101

[56] References Cited

U.S. PATENT DOCUMENTS

| 3,905,528 | 9/1975 | Maiocco. | |
| 4,052,320 | 10/1977 | Jakubowicz | 210/516 |
| 4,933,291 | 6/1990 | Daiss et al. | 422/72 |
| 4,935,147 | 6/1990 | Ullman et al. | 210/222 |

FOREIGN PATENT DOCUMENTS 8808138 12/1988 Fed. Rep. of Germany .

Primary Examiner—Robert A. Dawson
Assistant Examiner—David Reifsnyder
Attorney, Agent, or Firm—Young & Thompson

[57] ABSTRACT

Device for measuring off of a volume of a flowable material, comprising a centrifugable reservoir provided with a bottom, side-walls and an entrance opposite the bottom, and an occludable aperture which is spaced between the bottom and entrance both when the aperture is open and when the aperture is closed. The aperture can be closed for collecting an overmeasure of the material in the reservoir pressed towards the bottom thereof during a first centrifuge run and can be opened for discharging the excess volume of the material during a second centrifuge run such that an exactly predetermined volume of the material is retained in the reservoir between the aperture and the bottom.

7 Claims, 1 Drawing Sheet

DEVICE AND METHOD FOR THE QUANTITATION OF A VOLUME OF A SEDIMENT OR OF A VOLUME OF A FLUID WHICH DOES NOT FLOW EASILY

The present invention refers to a device for measuring off of a volume of a flowable material, comprising a centrifugable reservoir provided with a bottom, sidewalls and an entrance opposite the bottom. Measuring off of a volume of a material that flows easily is without difficulties. By using a pipette the desired quantitity can be dosed simply. However the quantitation of a volume of materials which do not flow easily does give problems. A pipette is less suitable because the sucking of an exact standardized quantity of this material into a pipette is not simple.

Also in the literature devices are described that can seperate fluids with good streaming properties in such ways semiquantitatively such as for instance plasma (patent document U.S. Pat. No. 3,905,528) or serum (patent document DE-U-8808138) from a sediment. However these devices are not constructed in order to measure off an exact known volume, let alone can these devices measure off exactly a volume of a fluid with poor streaming properties.

An example of such a material which does not flow easily is a sediment of red blood cells obtained after centrifuging blood to which an anticoagulant is added. The centrifuged mass of cells does not flow easily as only about 2 percent (v/v) of plasma remains between the cells. In case that an exact known volume of the red cell mass can be measured off, it is thereafter possible to carry out an exact measurement of compounds associated with that red cell mass. This is especially important for compounds that are little or only restrictively (saturable protein binding) solvable in plasma and which by measuring of plasma only are unsatisfactorily determined in blood. Among many possible examples we mention the hormone hydrocortisone, the free fatty acid with a short chain and also medicament dipropylaceticacid (valproate) and the drug phenytoin.

The quantitation of a volume of materials which do not flow easily does give problems. The use of a pipette is impossible because the sucking of an exact standardized quantity of such material into a pipette is unfeasable. Because a force considerably greater than gravity or vacuum pressure must be applied to propel a fluid with really poor streaming properties, devices constructed to measure off such fluids must contain a mechanism producing an exact and stable volume of the material in question, whereas, that volume is not to be influenced by the kind or degree of the applied force.

The aim of the invention hence is to give a device with which materials which do not flow easily can be quantitated simply and exactly. This acheived in that the device is provided with an occludable aperture situated between the bottom and the entrance, which aperture can be closed for collecting an overmeasure of the material in the reservoir pressed towards the bottom thereof during a first centrifuge run and which aperture can be opened for discharging the excess volume of the above collected material during a second centrifuge run such that an exact predetermined volume of the material is retained in the reservior between the aperture and the bottom.

The reservoir may be secured in a container provided with a receplacle into which the opening of the reservoir emerges, which container with reservoir are to be placed radially in a centrifuge rotor. The material to be flung out of the opening of the reservoir during centrifugation can be collected in the receptacle of the container. It is of importance that at the end of the procedure residue of the suspension can be found in or outside the reservior other than in the space formed by the border wall and the opening because any residue for instance at the container facing side of the reservoir near the opening will hamper the collection of the fixed volume of the sediment enclosed between the border wall and the opening. Also it is undesirable that a reservoir to be handled is on the outside contaminated with blood.

The opening in the reservoir can be closed in several ways. Preferably the container has an abutment surface facing away from the receptacle into which a passage emerges connected to the recipient, the reservoir has a supporting face to be placed opposite to that abutment surface of the container into which the aperture emerges, and between abutment surface and supporting surface a packing is provided to close the aperture.

In this context a suitable embodiment can be obtained if container and reservoir can cooperate by means of a screw connection in such a way that in a tightly fitted position the packing will close the aperture whereas in partly unscrewed or unfitted position a free flow of connection exists between the aperture of the reservoir and the passage in the container. The procedure of measuring the sediment of a suspension starts by centrifuging the reservoir tightly screwed down in its container. During this first centrifugation step the sediment will be collected in the readrally exterior part of the reservoir up to and beyond the aperture. Subsequently the aperture is opened as mentioned and in a second centrifugation step the superfluous part of the suspension and of the sediment is discharged. In a preferred embodiment of the invention the container has a rim protruding from the abutment surface and the reservoir has a circumferential part at the supporting surface that fits tightly within that rim.

When the device is radially placed on a planar centrifuge rotor and hence not in a swinging rotor, part of the material to be investigated might flow out of the reservoir before the centrifuge starts spinning. To counteract this a piston may be placed on top of the material present in the reservoir. In this way a loss of material will be prevented.

The measurement of material in a suspension can be successfully undertaken with the device here described in case the specific weight of that material is higher than of the rest of the suspension. In case the material has a specific weight similar to or lower than the rest of the suspension, then other methods must be applied to concentrate that part of the suspension, in the radially outer part of the reservoir before quantitative investigations on the concentrated particles with known volume can take place.

According to a variant of the invention a magnetic material in a suspension independent of the specific weight of the material can be measured by embodying the device in such a way that outside the reservoir fitted into its holder an apparatus is located for generating a radial magnetic field in such a manner that the material by the force of the magnetic field is pressed to the outer border wall of the reservoir.

Preferably the device will be used to measure a certain volume of particles from a suspension, such as red blood corpuscles in blood. According to the invention the procedures starts centrifuging (about 10000 g) with the reservoir and container tightly screwed together in order to separate the heavy particles of the suspension and to press the erythrocytes maximally together, subsequently the reservoir is partly unscrewed from the holder and then in a second centrifugation step the superfluous sediment is removed through the aperture and the passage. Between the first and second centrifugation step a plasma sample can be taken. Becasue the opening in the reservoir has to be tightly closed during the first centrifugation step a vacuum may be maintained in the total device of reservoir and container. This vacuum can be desirable in the case of bloodsampling (vacutainer).

The invention will be explained further with reference to a tested embodiment:

FIG. 1 shows a perspeative view of a centrifuge with a planar rotor, provided with the device according to the invention.

Figure 2:
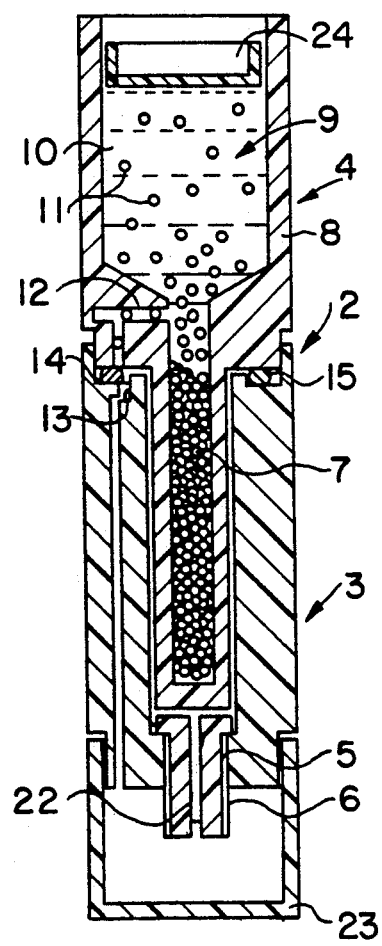

FIG. 2 shwos a cross-section of the device with the opening in the reservoir locked.

Figure 3:
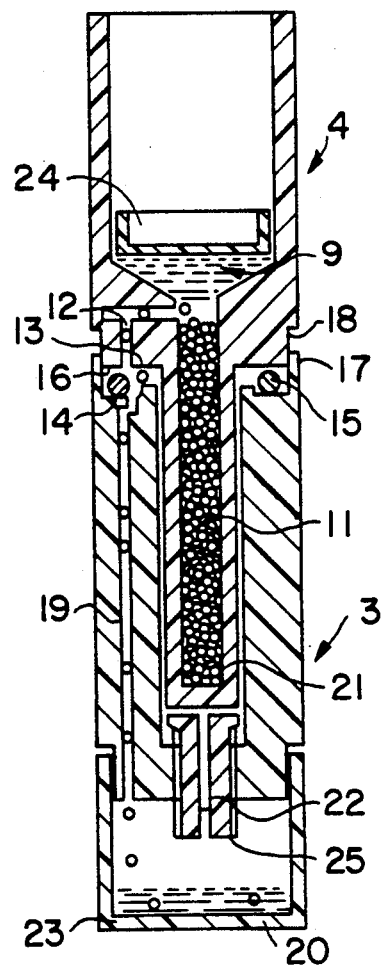

FIG. 3 shows a cross-section of the device with the opening in the reservoir free.

The centrifuge as depicted in FIG. 1 is known and contains a planar rotor 1 in which at least two devices of the present invention can be placed diametrically opposite each other. The rotor 1 revolves in such a way that the material contained in the devices 2 is pressed radially to the exterior.

As depicted in FIG. 2 every device 2 consists of a holder 3 and a reservoir 4. Using the screw-threads 5 and 6 the reservoir 4 is fixed into the holder 3. Reservoir 4 is a cylindrical body with a first reservoir part with a relatively small diameter 7 and a second larger reservoir part 8 in which the material to be investigated 9 is disposed. The material 9 is for instance a sludge 10 which does not flow easily, in which heavier particles 11 can be discerned. As an example the sludge is blood in which the heavier particles are erythrocytes. To collect an exact and known volume of erythrocytes the reservoir 4 is centrifuged with the aperture annex small side channel 12 closed by the o-ring 15 as depicted in FIG. 2. By the centrifugation at about 10000 g the erythrocytes 11 are pressed into the first reservoir part with the small diameter 7. At the end of the first centrifugation step the reservoir part 7 as well as the adjoining part of the reservoir 8 is filled with maximally compressed erythrocytes 11 together with @ 2% v v of plasma between these red cells.

As can be seen in FIG. 2 and as mentioned the reservoir part 7 has an aperture 12, opening through the supporting surface 13 of the reservoir 4. This supporting surface 13 faces the abutment surface 14 of the holder 3. Between the supporting surface 13 and the abutment surface 14 an o-ring seal 15 is situated. In the case the reservoir 4 is tightly screwed into the holder 3 the o-ring packing 15 will close the aperture 12 of the reservoir and consequently the material 9 cannot flow away out of the reservoir 4. On top of the material 9 a piston 24 can be placed in case that the device must be placed horizontally on a planar centrifugal rotor. This piston prevents the outflow of material 9 from a too well filled reservoir part 8 before spinning of the centrifuge. A swing out rotor and/or the filling of the large part 8 of the reservoir 4 with an volume of blood makes the piston 24 unnecessary.

In FIG. 3 the reservoir 4 is screwed somewhat out of the holder 3 and hence in the second centrifugation step the o-ring 15 does not close the aperture 12. Therefore components 10 and 11 of material 9 can for instance by centrifugal force be pressed into the space 16 formed by supporting surface 13, abutment surface 14 and the edge 17 protruding with respect to the abutment surface, in which the narrowed part 18 of part 8 of the reservoir 4 fits tightly. Preceding this second centrifugation step the supernatant plasma is pipetted off for independent analysis. From space 16 components 10 and 11 flow into channel 19 and subsequently in the receptacle 20 at the radially outer side of the holder 3. The sediment located between the bottom 21 of the more narrow part 7 of the reservoir 4 and aperture 12 cannot escape, however the material located above the side channel and aperture 12 will so. This material will be the excess erythrocytes and remaining plasma. The short second centrifugation step lasts until the material above the aperture is transferred to the receptacle 20. Thereafter the first reservoir part 7 contains an exact known volume of particles and some included fluid because the volume between bottom 21 of reservoir part 7 and the aperture of the overflow is fixed and known and because the included fluid between maximally compressed erythrocytes is constant. For an erythrocyte sediment obtained with a centrifugal force of about 10000 g the intercellular fluid is about 2% vv. After the collection of a sediment with a known volume this mass can be easily and quantitatively removed from the reservoir 4 by centrifuging only the reservoir upside down in a tapered test tube.

As is depicted in FIGS. 2 and 3 there is a venting channel 22 opening into the receptacle 20 in the reservoir part 7 of the reservoir 4. This channel starts into the receptacle 20 protruding front surface 25 of the reservoir 4 and proceeds through the part with the screw-thread of reservoir 4 and emerges subsequently radially above the screw-thread and at two sides of the part 7. By this air venting channel 22 it is prevented that by screwing the reservoir 4 down into the holder 3 an air pressure builds up in the receptacle 20 as a consequence of a sealing off by the joining screw-threads. Such an air pressure must always be avoided as the flow of material through aperture 12 and channel 19 might be hampered.

The receptacle 20 can be formed by a receptacle 23 that can be fitted to or loosened from the holder 3 for instance with screw-thread, facilitating cleaning of the device.

I claim:

1. Device for measuring off of a volume of a flowable material, comprising a centrifugable reservoir provided with a bottom, side-walls and an entrance opposite the bottom, and an occludable aperture which is spaced between said bottom and said entrance both when said aperture is open and when said aperture is closed, whereby said aperture can be closed for collecting an overmeasure of the material in the reservoir pressed towards the bottom thereof during a first centrifuge run and can be opened for discharging an excess volume of the material during a second centrifuge run such that an exactly predetermined volume of the material is retained in the reservoir between the aperture and the bottom after said second centrifuge run.

2. Device according to claim 1, and a receptacle coaxial with said reservoir and communicating with said aperture to collect material which passes through said aperture.

3. Device according to claim 2, the reservoir being in two interfitting parts which can be moved toward and away from each other, and a seal disposed between said parts and closing said aperture when said parts are moved toward each other and opening said aperture when said parts are moved away from each other.

4. Device according to claim 3, and screw threads interconnecting said parts for moving said parts toward and away from each other.

5. Device according to claim 3, and vent means for permitting air within said receptacle to escape when said parts are moved toward each other.

6. A method for measuring off a volume of a flowable material in a centrifugable reservoir having a bottom, side walls and an entrance opposite the bottom and an occludable aperture which is spaced between said bottom and said entrance both when said aperture is open and when said aperture is closed, comprising introducing flowable material through said entrance into said reservoir in a quantity such that said flowable material extends on both sides of said aperture, centrifuging the reservoir with the aperture closed, opening the aperture, and again centrifuging the reservoir with the aperture open, thereby to expel from the reservoir flowable material in excess of that which occupies the reservoir between said aperture and said bottom.

7. A method for measuring off a volume of a flowable material in a centrifugable reservoir having a bottom, side walls and an entrance opposite the bottom and an occludable aperture which is spaced between said bottom and said entrance both when said aperture is open and when said aperture is closed, comprising introducing flowable material through said entrance into said reservoir in a quantity such that said flowable material extends on both sides of said aperture, centrifuging the reservoir with the aperture closed, opening the aperture, and applying overpressure to the flowable material in the reservoir so as to expel through said aperture material in excess of the material between said aperture and said bottom.

* * * * *